(12) United States Patent
Abri et al.

(10) Patent No.: US 8,870,141 B2
(45) Date of Patent: Oct. 28, 2014

(54) ADJUSTABLE HOLDING APPARATUS FOR AN ENDOSCOPE

(75) Inventors: Omid Abri, Berlin (DE); Josef Reinauer, Inzigkofen (DE)

(73) Assignee: Karl Storz GmbH & Co. KG (DE)

( * ) Notice: Subject to any disclaimer, the term of this patent is extended or adjusted under 35 U.S.C. 154(b) by 19 days.

(21) Appl. No.: 13/409,903

(22) Filed: Mar. 1, 2012

(65) Prior Publication Data
US 2012/0223199 A1 Sep. 6, 2012

(30) Foreign Application Priority Data

Mar. 1, 2011 (DE) .......................... 10 2011 004 926

(51) Int. Cl.
| | | |
|---|---|---|
| *F16M 11/12* | (2006.01) | |
| *F16M 11/14* | (2006.01) | |
| *F16M 11/24* | (2006.01) | |
| *F16M 11/20* | (2006.01) | |
| *F16M 13/02* | (2006.01) | |
| *A61B 1/00* | (2006.01) | |
| *A61B 19/00* | (2006.01) | |

(52) U.S. Cl.
CPC ......... F16M 11/14 (2013.01); F16M 2200/024 (2013.01); F16M 11/24 (2013.01); F16M 11/2014 (2013.01); *F16M 2200/063* (2013.01); *F16M 11/2064* (2013.01); F16M 13/022 (2013.01); F16M 11/2092 (2013.01); *A61B 1/00149* (2013.01); *A61B 2019/263* (2013.01); *A61B 19/26* (2013.01)
USPC .................. 248/281.11; 248/280.11; 248/585; 248/276.1; 403/93

(58) Field of Classification Search
CPC ....... F16M 11/06; F16M 11/08; F16M 11/10; F16M 11/12; F16M 11/121; F16M 11/20; F16M 11/2007; F16M 11/2014; F16M 11/2021; F16M 11/2023; F16M 11/2042; F16M 2200/021; F16M 2200/04; F16M 2200/047; F16M 2200/048; F16M 2200/063; A61B 2019/26; A61B 2019/264; A61B 2019/265; A61B 2019/266
USPC .................. 248/585, 281.11, 292.11, 292.13, 248/276.1, 280.11; 403/84, 91–94, 103
See application file for complete search history.

(56) References Cited

U.S. PATENT DOCUMENTS

| | | | | |
|---|---|---|---|---|
| 5,020,933 A | * | 6/1991 | Salvestro et al. ............... | 403/90 |
| 5,213,293 A | * | 5/1993 | Muentener et al. ...... | 248/123.11 |

(Continued)

FOREIGN PATENT DOCUMENTS

| | | |
|---|---|---|
| DE | 29511900 U1 | 9/1995 |
| DE | 10141225 A1 | 4/2003 |

(Continued)

OTHER PUBLICATIONS

German Search Report; Application No. DE 10 2011 004 926.6; Issued: Oct. 11, 2011; 5 pages.

(Continued)

*Primary Examiner* — Jonathan Liu
*Assistant Examiner* — Guang H Guan
(74) *Attorney, Agent, or Firm* — St. Onge Steward Johnston & Reens LLC (57) ABSTRACT

An adjustable holding apparatus for an endoscope or other medical device having a proximal end and a distal end, the adjustable holding apparatus having a device for holding an endoscope or other medical device that includes a number of arm segments between the proximal end and the distal end, a number of lockable joints that each connect two of the number of arm segments with one another in jointed fashion, and a compensation device for at least partial compensation of the weight impact of the holding apparatus in a pivoting or sliding of at least one arm segment in the vertical direction.

11 Claims, 2 Drawing Sheets

(56) References Cited

U.S. PATENT DOCUMENTS

| | | | |
|---|---|---|---|
| 5,288,043 A * | 2/1994 | Tigliev | 248/123.11 |
| 5,609,316 A * | 3/1997 | Tigliev | 248/123.11 |
| 5,748,366 A * | 5/1998 | Yasunaga et al. | 359/368 |
| 5,824,007 A | 10/1998 | Faraz et al. | |
| 5,825,536 A * | 10/1998 | Yasunaga et al. | 359/384 |
| 5,862,723 A * | 1/1999 | Rowlands | 81/177.9 |
| 6,471,165 B2 * | 10/2002 | Twisselmann | 248/123.11 |
| 6,491,273 B2 * | 12/2002 | King et al. | 248/276.1 |
| 6,543,914 B2 * | 4/2003 | Sander | 362/401 |
| 6,591,690 B1 * | 7/2003 | Crockford | 73/760 |
| 6,632,170 B1 | 10/2003 | Bohanan et al. | |
| 6,788,018 B1 | 9/2004 | Blumenkranz | |
| 7,283,296 B2 * | 10/2007 | Nozawa et al. | 359/384 |
| 7,314,200 B2 * | 1/2008 | Bally et al. | 248/276.1 |
| 7,420,731 B2 * | 9/2008 | Piontkowski | 359/382 |
| 8,038,108 B2 * | 10/2011 | Yasunaga et al. | 248/123.2 |
| 8,177,181 B2 * | 5/2012 | Papendieck et al. | 248/281.11 |
| 8,448,909 B2 * | 5/2013 | Metelski | 248/281.11 |
| 2002/0121577 A1 * | 9/2002 | Metelski | 248/123.11 |
| 2002/0177857 A1 | 11/2002 | Otsuka et al. | |
| 2006/0126167 A1 | 6/2006 | Piontkowski | |
| 2006/0206144 A1 * | 9/2006 | Miersch | 606/205 |
| 2010/0139436 A1 | 6/2010 | Kawashima et al. | |
| 2012/0223199 A1 * | 9/2012 | Abri et al. | 248/280.11 |

FOREIGN PATENT DOCUMENTS

| | | |
|---|---|---|
| DE | 602004003318 T2 | 3/2007 |
| EP | 1152182 A1 | 11/2001 |
| EP | 1959184 A2 | 8/2008 |
| WO | 8103054 A1 | 10/1981 |
| WO | 9314704 A1 | 8/1993 |
| WO | 03017859 A1 | 3/2003 |
| WO | 2008040537 A1 | 4/2008 |

OTHER PUBLICATIONS

European Search Report; Application No. EP 12 15 7609; Issued: May 8, 2012; Mailing Date:May 16, 2012; 13 pages.

* cited by examiner

ADJUSTABLE HOLDING APPARATUS FOR AN ENDOSCOPE

CROSS-REFERENCE TO RELATED APPLICATIONS

The present application claims priority of German patent application No. 10 2011 004 926.6 filed on Mar. 1, 2011, the content of which is incorporated herein by reference.

FIELD OF THE INVENTION

The present invention relates to an adjustable holding apparatus for an endoscope or other medical apparatus.

BACKGROUND OF THE INVENTION

In surgical and other medical interventions in which an endoscope is used, it can be advantageous not to hold the endoscope manually but rather by means of a holding apparatus. As a result, medical staff can be relieved or even reduced. In addition, a mechanical holding apparatus can hold an endoscope for any desired time period, in precise manner, at a determined spot and with a determined orientation, without staff becoming fatigued in the process.

In patent DE 295 11 900 U1, a holding apparatus for surgical purposes is described, which can be fastened on a holding track of an operating table. Brackets are pivotably connected with one another by ball joints. A locking device is associated with each ball joint. The ball is locked in its position, to prevent rotation, by means of the pressure of a spiral spring that presses a cup against a ball of the ball joint. The locking of all ball joints can be released simultaneously by means of a shut-off valve on the front bracket. The locking of a single ball joint can be released by means of a release lever.

In patent WO 93/14704, an apparatus for positioning a surgical instrument is described. A ball joint with a ball can be blocked by means of a pneumatic actuator. A scissor-type lever apparatus to reinforce the power of the pneumatic actuator is positioned between the pneumatic actuator and a beaker that acts on the ball.

A disadvantage of a holding apparatus, as it is described for example in patent DE 295 11 900 U1, consists in the fact that upon abrupt, non-controllable release of the locking of all ball joints, it is possible to avoid a jerking motion of the holding apparatus only with considerable practice on the part of medical staff, on account of its weight and the weight of the object that is being held.

SUMMARY OF THE INVENTION

It is an object of the present invention to provide an improved holding apparatus for an endoscope or other medical device.

This objected is achieved by providing an adjustable holding apparatus for an endoscope or other medical device that includes a proximal end, a distal end with an apparatus for holding an endoscope or other medical device, a number of arm segments between the proximal end and the distal end, a number of lockable joints that each connect two of the number of arm segments with one another in jointed fashion, and a compensation device to compensate at least in part for the weight impact of the holding apparatus in a manual pivoting or sliding of at least one arm segment in the vertical direction.

The proximal end of the adjustable holding apparatus is configured in particular for fastening onto an operating table. For this purpose, on the proximal end of the holding apparatus a clamping device, for example, is provided that is compatible with the steel tracks that are present on the sides of many operating tables.

Alternatively, the proximal end of the adjustable holding apparatus can be configured for direct or indirect fastening to apparatus of a ceiling of an operating room or other room. In particular, the proximal end of the adjustable holding apparatus is configured to be fastened to a ceiling bracket, which itself can be of rigid or adjustable configuration.

For example, the adjustable holding apparatus comprises on its proximal end a plug-in bolt that can be configured in order to be inserted alternatively into the aforementioned clamping device for fastening to an operating table or into a ceiling bracket. For this purpose, the plug-in bolt in particular comprises a cylindrical or essentially cylindrical portion that can be fastened to the clamping device and/or to the ceiling bracket by clamping or other means in a corresponding recess. To reinforce a reliable bracket—in particular in the case of a fastening to a ceiling bracket—the plug-in bolt can comprise in its cylindrical portion a curve, a groove (in particular, a surrounding groove) or another concave area that makes a form-locked connection possible.

The apparatus for holding an endoscope or other medical device on the distal end of the adjustable holding apparatus includes, in particular, two jaws that can be pressed together by a spring or screw. The two jaws, in particular with respect to their structure and material, are adapted to the typical cross-sections of the shafts of endoscopes in order to hold them securely and without damage occurring.

One arm segment of the holding apparatus encloses, in particular, a straight or curved rigid portion of the holding apparatus. The holding apparatus is made predominantly adjustable as a result of the lockable joints, each of which comprises one or more degrees of freedom. The compensation device grips, in particular, onto one or more arm segments and/or onto one or more joints, in order to compensate at least in part for the weight impact of the arm segment on the compensation device and/or the weight impact of arm segments distally situated from the compensation device. In addition, the compensation device can be configured in order to compensate for the weight impact of an endoscope or other medical device. The compensation device can be adjustable for use with different types of endoscopes or other medical devices, in order to allow the different masses and weight impacts of different endoscopes or other medical devices to be taken into account.

The term "compensation for weight impact" is understood in particular to mean a predominant compensation so that the non-compensated or over-compensated part of the weight impact makes up only a small portion of the weight impact, for example a maximum of 20 percent or a maximum of 10 percent or of 5 percent. The compensating force exerted by the compensation device thus amounts to between 80 and 120 percent of the weight impact, or between 90 and 110 percent of the weight impact or between 95 and 105 percent of the weight impact. In particular, the extent of the difference between weight impact and compensation force is so small that is not sufficient to overcome the static friction in the corresponding joint or joints if it or they are not locked.

It is obvious that the weight impact and compensation forces generate in the corresponding joints sufficient rotary moments for which the same also applies.

Contrary to a simple locking of a joint, the compensation device is intended and configured to compensate the weight impact at least partly, even in the event of pivoting in the vertical direction. The compensation device is therefore a device that is partly or completely independent of the locking and that can also at least partly compensate for the weight impact of the holding apparatus or of one or more arm segments and/or of an endoscope or other medical device, even with the locking released.

Characteristics, variants and embodiments of the adjustable holding apparatus, as illustrated below, show in particular how the adjustable holding apparatus can be configured in such a way that even a single compensation device on an arm segment or on a joint makes possible an at least partial compensation of the weight impact of the entire holding apparatus. Alternatively, compensation devices can be provided on several arm segments and/or on several joints.

The compensation device of the adjustable holding apparatus makes it possible that upon releasing the locking of the joints in a non-abrupt manner, the entire weight impact of the adjustable holding apparatus, in particular of its distal arm segments, and of the endoscope must be assumed by medical staff. In working with a conventional holding apparatus, medical staff anticipates the weight impact and try to compensate for it at the time of releasing the locking. However, his assumes, first, that the medical staff are skillful and practiced in using the holding apparatus and, second, that there has been a high degree of concentration on the process. Every time the weight impact is estimated erroneously, or every time the actual weight impact that is to be compensated departs from the expectations of medical staff, the result is an abrupt motion of the distal end of the conventional holding apparatus in a downward or upward direction. At that same moment, if an endoscope that has been inserted into a patient's natural or artificial bodily opening is being held by the holding apparatus, the resulting abrupt movement of the endoscope can have a traumatizing effect.

The compensation device of the present adjustable holding apparatus can at least clearly reduce the weight impact that is to be compensated by the medical staff after release of the locking. With appropriate sizing or adjustment of the compensation device, no force, or nearly none, is required also after release of the locking in order to manually hold the distal end of the adjustable holding apparatus. Undesired movements of the distal end of the adjustable holding apparatus, and in particular of an endoscope held by it, can be markedly reduced or prevented as a result. This reduces, on the one hand, the risk of injury to the patient and, on the other hand, the extent of the concentration on the process on the part of medical staff. As a result, the compensation device makes possible a more relaxed and less tiring activity by medical staff and a reduction or complete avoidance of a trauma to the patient owing to an involuntarily moved endoscope. Both factors, directly and indirectly, have advantages for the patient as well as economic benefits.

Many conventional holding apparatuses are based on numerous ball joints and the attempt to have the holding apparatus as closely as possible resemble the human arm with its numerous degrees of freedom. More precise observation, however, shows that the high degree of mobility of the human arm, considered virtually ideal, is absolutely not achieved, as a rule. The reason, above all, is that a range of movement of clearly more than about +/−40 degrees is scarcely possible with a single ball joint. On the other hand, a conventional holding apparatus with several ball joints typically offers numerous degrees of freedom, which are not at all required. For example, a ball joint as a rule comprises one degree of freedom of rotation around the axis of symmetry of the joint, which as a rule is required in any case at one or two joints of the adjustable holding apparatus.

Altogether, dispensing at least for the most part with the use of ball joints makes possible an easier integration of a compensation device as described here. Several of the characteristics and embodiments of the compensation device described hereinafter can also be realized by one ball joint, although with clearly greater expense.

In an adjustable holding apparatus as described here, an arm segment can be configured in the form of a parallelogram link.

In particular, the arm segment closest to the proximal end, or the first arm segment from the proximal end of the adjustable holding apparatus that is not purely vertically aligned, is configured in the form of a parallelogram link. The parallelogram link allows a vertical sliding of the distal end of the arm segment that is configured in the form of a parallelogram link and of the distally contiguous arm segments.

It is already possible, with a single arm segment configured in the form of a parallelogram link, to achieve a sufficient vertical slidability of the distal end of the adjustable holding apparatus, even when further arm segments no longer have any vertical degrees of freedom. Alternatively, two or more arm segments can each be configured in the form of a parallelogram link.

An advantage of the parallelogram link consists in the fact that the distal end of the arm segment configured in the form of a parallelogram link, when slid vertically with respect to its proximal end, is pushed only in the vertical direction and to a restricted extent also in the horizontal direction but is not pivoted or tipped in the vertical direction. Also the arm segments positioned distally from the arm segment configured in the form of a parallelogram link are therefore not pivoted or inclined in vertical direction but only slid in the vertical and horizontal directions. If the compensation device is provided at the arm segment that is configured in the form of a parallelogram link, the weight impact that is to be compensated by the compensation device can therefore be independent of additional degrees of freedom of the adjustable holding apparatus.

In particular, the configuration of one or more arm segments in the form of a parallelogram link, and the arrangement of one compensation device at each arm segment configured in the form of a parallelogram link, thus makes possible a particularly precise compensation of the weight impact and thereby an especially sensitive manual manipulation of the distal end of the adjustable holding apparatus.

With an adjustable holding apparatus in which an arm segment is configured in the form of a parallelogram link, the compensation device includes a spring or other elastic element at the arm segment configured in the form of a parallelogram link.

In particular, the compensation device includes a spring or other elastic element that is positioned in the arm segment configured in the form of a parallelogram link, for example between two parallel guide bars of the parallelogram link. Also in the case of an adjustable holding apparatus as described here, in which no arm segment is configured in the form of a parallelogram link, the compensation device in particular includes a spring or other elastic element. In all cases the spring can be a spiral spring, leaf spring, gas pressure spring, or other type. Other elastic elements are, for example, elastically reshapable bodies of rubber or an elastomer. The arrangement of a spring or other elastic element on an arm segment configured in the form of a parallelogram link can make possible a partial or complete compensation of the weight impact of the holding apparatus that can be realized at reasonable cost and is simultaneously precise and robust.

In an adjustable holding apparatus as described here, the compensation device includes in particular no mechanical power drive.

In particular, the compensation device includes no electrical, magnetic, hydraulic or pneumatic power drive.

In an adjustable holding apparatus as described here, in particular, one or more arm segments of the number of arm segments can pivot only around vertical, or essentially vertical, axes.

In particular in the configuration of an arm segment in the form of a parallelogram link that allows vertical sliding, the holding apparatus, in particular the distal end of the holding apparatus, can be sufficiently adjustable or movable even when several or even all, or all additional, arm segments can pivot only around vertical or essentially vertical axes. Configuration of one or more arm segments or of associated guide bars in such a way that the arm segment or segments can pivot only around vertical or essentially vertical axes makes it unnecessary to compensate the weight impact of this arm segment or these arm segments (as well as of arm segments positioned distally from them) at the corresponding joints. In other words, compensation of the weight impact is required only on the arm segments that can pivot not only around vertical or essentially vertical axes. In the simplest case, compensation is required only on an arm segment that is configured, for example, in the form of a parallelogram link. This makes possible simultaneously a simple, cost-effective structure of the adjustable holding apparatus and, ideally, a complete compensation of the weight impact with the advantages described above.

In an adjustable holding apparatus as described here, in particular, a joint is configured on a predetermined arm segment to allow pivoting around a horizontal axis, and additional joints are configured, in each case, only for pivoting around an axis that is perpendicular to the horizontal axis.

In the case of the configuration of an arm segment, as described above, in the form of a parallelogram link, the joints bordering on this arm segment are configured to allow pivoting around a horizontal axis. As already mentioned, additional joints or almost all, or all additional, joints can each be configured to pivot around a vertical or essentially vertical axis, and thus an axis that is perpendicular to the horizontal axis.

Alternatively, a predetermined arm segment can pivot around a horizontal axis, in particular only around a horizontal axis, and additional arm segments are connected with the predetermined arm segment or with one another by joints that each are configured only for pivoting around an axis that is perpendicular to the horizontal axis. The farther in the distal direction an arm segment is positioned, the smaller is the effect of pivoting of the arm segment on the position of the center of gravity of the adjustable holding apparatus. For a predetermined arm segment that is configured to pivot around a horizontal axis, the farther it is positioned in the proximal direction, the smaller is the angle by which the predetermined arm segment and all arm segments positioned distally from it must be pivoted around the horizontal axis in order to perform a predetermined vertical sliding of the distal end of the adjustable holding apparatus.

As long as arm segments distally located from the predetermined arm segment must be pivoted around their associated axis only by small angles, the position of the center of gravity of the adjustable holding apparatus also changes only slightly, and the compensation device can substantially compensate the weight impact of the holding apparatus. As long as the predetermined arm segment and the arm segments distally located from the predetermined arm segment must be pivoted only by a small angle around the horizontal axis to achieve vertical sliding of the distal end of the adjustable holding apparatus, the departure from the vertical axis of the pivot axes associated with the arm segments located distally from the predetermined arm segment, and the rotary moments resulting from gravity, can be small. In an adjustable holding apparatus with a predetermined arm segment that can pivot around a horizontal axis and with additional joints that are each configured only to pivot around an axis perpendicular to the horizontal axis, in releasing the locking of the joints the force required to hold the distal end of the adjustable holding apparatus, and possibly of an endoscope, thereon can thus be small.

An adjustable holding apparatus as described here can, instead of or in addition to an arm segment configured in the form of a parallelogram link or a capacity to pivot around a proximally positioned horizontal axis, be vertically slidable by means of a linear guide, for example by means of a telescopable vertical arm segment. In this case as well, additional arm segments can be configured in order to be pivotable only around vertical or essentially vertical axes. In this case the compensation device is positioned on the vertical linear guide so that the weight impact of the adjustable holding apparatus can be partly or completely compensated in all positions or configurations of the adjustable holding apparatus.

In an adjustable holding apparatus as described here, a lockable joint can include a locking device to lock the joint, a power drive device to actuate the locking device, and a gear that transmits a smaller force and a greater path on the power drive device into a greater force and a smaller path on the locking device.

The locking device includes, for example, a smooth or corrugated surface that can be contiguous with a correspondingly configured surface of an axle in order to prevent or restrict a relative rotation of the axle and the locking device. For this purpose the locking device is, in particular, slidable in a direction that is radial with respect to the axle. The power drive device includes, for example, an electromotor, an electromagnet, a hydraulic cylinder or a pneumatic cylinder. The gear can be, for example, a tooth wheel gear, coupling gear or a gear in which sliding parts contiguous with several surfaces can transmit forces and paths between the surfaces Use of a gear between the power drive device and the locking device, for example in the case of a pneumatic or hydraulic power drive device, makes it possible to use a smaller pressure to generate a predetermined force to actuate the locking device. For example, a gear can make it possible to use the compressed air that is commonly provided in operating rooms at a predetermined pressure level and/or with the pneumatic cylinder at a smaller cross-section.

The gear can be, in particular, a locking gear.

It can be advantageous, especially with a locking device acting in form-locked manner, to use a locking gear in which the transmission or reduction ratio and the friction inside the locking gear are sized in such a way that a small force at the input of the gear is sufficient to prevent a movement at the output of the gear, even with a great counter-force. The force required to release or unlock the locking can be smaller or essentially smaller in this case than the force required to overcome the locking.

In an adjustable holding apparatus with a gear as described here, the lockable joint can in addition include a spring or other elastic element that is coupled with the locking device in such a way that a force exerted by the elastic element causes a locking of the joint.

In this case the power drive device is configured to release the lock. In case of failure of the energy or power supply required for the power drive device, the lockable joint remains locked. For example, the adjustable holding apparatus remains locked even in the absence of the compressed air.

In an adjustable holding apparatus in which a lockable joint includes a locking device, a power drive device and a gear, the gear in particular includes a sliding surface on the locking device, a sliding surface on the power drive device, a guide and a sliding piece that is contiguous with the sliding surface of the power drive device and is controlled by the guide.

The sliding piece can be, for example, a cylindrical body. The guide is, for example, an additional sliding surface on a housing body that encloses the gear. The sliding surfaces can each be either flat or curved. Each sliding surface can be flat or curved in the foreseen sliding direction of the sliding piece. The reduction or transmission ratio of the gear and, in some cases, its properties as locking gear are especially dependent on the angles between the sliding surfaces and the direction determined by the guide in areas in which the sliding piece touches the sliding surface of the locking device, the sliding surface of the power drive device and the guide. The properties of the gear as locking gear are, in addition, dependent on the tribological properties of the involved surfaces, in particular on static and sliding friction between the involved surfaces.

If the sliding surface of the locking device, the sliding surface of the power drive device are each level and the guide is straight, the transmission or reduction ratio and, in some cases, the properties of the gear as locking gear are independent of the positions of the locking device and power drive device. Owing to a curvature of one or both sliding surfaces on the locking device and power drive device and/or owing to a curvature of the guide, there can be a dependency of the transmission or reduction ratio and in some cases dependency of the properties as locking gear on the positions of the locking device and power drive device.

Hereinafter, the angle between the surface normals of the sliding surface of the locking device and the surface normals of the sliding surface of the power drive device is designated as the first angle. The angle between the surface normals of the sliding surface of the locking device and the normals on the direction determined by the guide (in particular, surface normals of the sliding surface that constitutes the guide) is referred to as the second angle. The angle between the normals on the direction determined by the guide and the surface normals of the sliding surface on the power drive device is referred to as the third angle. The surface normals are understood in each case to refer to the normal of the border surface pointing away from the corresponding body. The normals on the direction determined by the guide refer in each case to the normal that lies in a plane with the surface normals of the sliding surface being referred to. In the case of curved sliding surfaces and/or a curved guide, these refer to surface normals or normals in the areas in which the sliding piece touches the sliding surfaces or the guide.

It has proved particularly advantageous to use a configuration of the gear in which the first angle is greater than the second angle and the second angle is greater or much greater than the third. An angle is greater than another angle, in particular, when the difference of the angles is considerable, in particular equal to at least 5 degrees or at least 10 degrees or at least 15 degrees. An angle is considered, in particular, to be much greater than another angle when the difference in angles equals at least 30 degrees or at least 40 degrees.

The first angle, in particular, lies in the range between 130 and 170 degrees or in the range from 140 to 160 degrees. The second angle, in particular, lies in the range from 120 to 140 degrees. The third angle is, in particular, in the range from 60 to 100 degrees or in the range from 70 to 90 degrees.

The gear as described here with a sliding piece situated between a guide and two sliding surfaces can constitute a locking gear that is especially simple in construction and robust between the power drive device and the locking device. For this purpose, in particular, the aforementioned angles and the friction angles for the material pairs that slide on one another are attuned to one another. In particular with a form-locked locking by means of fluting on the locking device and, for example, an associated surface of an axle, the described gear can be executed in such a way that the force applied by the power drive device to insert the locking device is considerably smaller than the force with which the locking device is held in the locked position.

An adjustable holding apparatus as described here can include an unlocking device with a push-button that is associated with a single lockable joint to release the lock of the associated lockable joint by manual pressure on the push-button.

In particular when the force applied to the push-button is reinforced by one of the aforementioned gears between the power drive device and the locking device, a relatively small force on the push-button can be sufficient to release the lock. For this purpose the push-button acts on the power drive device, in particular, directly or indirectly. It can be advantageous to provide two push-buttons situated opposite one another, both of which act on the power drive device by releasing the lock. The two push-buttons are then, in particular, positioned in such a way that can be pressed together by the thumb and by the forefinger or middle finger of one of a medical staffer's hands in order to release the lock of the associated lockable joint.

Releasing a lock of a joint by pressure on a push-button or simultaneous pressure on two push-buttons can be especially ergonomic. In particular, this allows for markedly easier and more rapid actuation in comparison, for example, with the lever device described in patent WO 93/14704.

An adjustable holding apparatus as described here can include a number of unlocking devices as described above, which are each associated with a lockable joint.

The adjustable holding apparatus is further configured, in particular, to lock all or almost all lockable joints by means of a single control device, or to release all or almost all stops simultaneously. In addition, by means of the number of unlocking devices, the respective associated lockable joints can be manually unlocked individually. The number of unlocking devices can thus provide a redundancy in case of failure of the power drive devices, and an additional flexibility in locking or releasing the lock of individual joints.

BRIEF DESCRIPTION OF THE DRAWINGS

Embodiments are described in greater detail below with reference to the appended drawings, which are as follows.

DETAILED DESCRIPTION OF THE INVENTION

Figure 1:
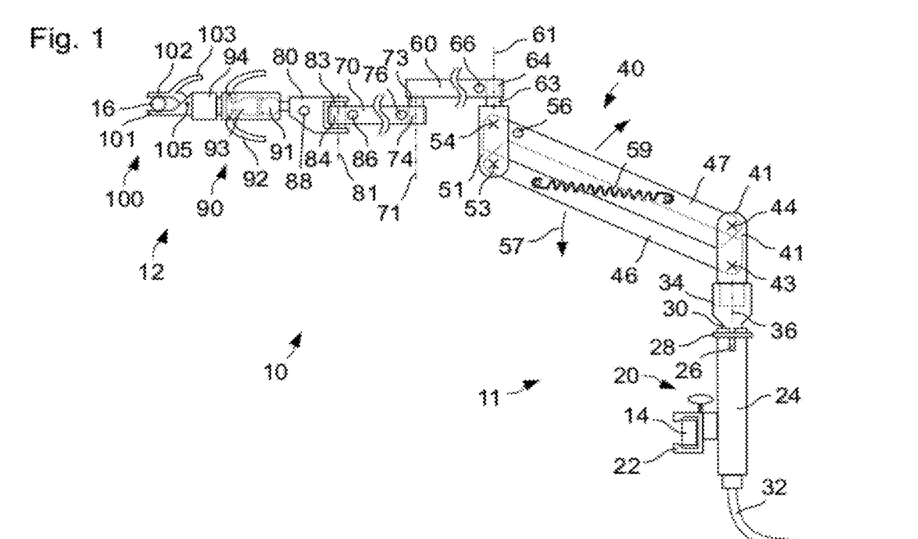
FIG. 1 shows a schematic depiction of an adjustable holding apparatus.

FIG. 1 shows a schematic depiction of an adjustable holding apparatus 10 with a proximal end 11 and a distal end 12. The adjustable holding apparatus 10 is configured to be fastened at the proximal end 11 on a fastening track 14 of an operatic table, not shown in FIG. 1, and to hold an endoscope 16 on its distal end 12. The endoscope 16 is depicted in FIG. 1 by a circular-shaped cross-section of a shaft, by way of example.

On the proximal end 11 the adjustable holding apparatus 10 comprises a holding segment 20 with a clamping device 22. The clamping device 22 is, in particular, configured as a screw clamp. The holding segment 20 also includes a vertical tube 24 that is connected with the clamping device 22, in particular rigidly connected by welding or other means. On its upper end the tube 24 comprises one or more slits 26 running parallel to its axis and a tensioning device 28.

The adjustable holding apparatus 10 further includes a vertical arm segment 30 whose lower, tube-shaped portion is positioned in the vertical tube 24 of the holding segment 20 and can be locked in place there at virtually any desired height by means of the tensioning device 28. The lower end of the vertical arm segment 30 is connected with a compressed air hose 32. At least the lower portion of the vertical arm segment 30, positioned in the vertical tube 24 of the holding segment 20, can be configured as a pressure reservoir for compressed air supplied by the compressed air tube 32. A chuck 34 with an axis of symmetry 36 is provided on the upper end of the vertical arm segment 30.

The adjustable holding apparatus 10 further includes an arm segment 40 configured as a parallelogram link. The arm segment 40 configured as a parallelogram link includes a stationary double joint 41, a first guide bar 46, a second guide bar 47, and a slidable double joint 51. The lower end, indicated in broken lines, of the stationary double joint 41 is configured to be held in the chuck 34. In particular, the lower end of the stationary double joint 41 is configured as a plug-in bolt with a cylindrical or essentially cylindrical portion that can be held by clamping in the chuck. When the chuck 34 is not locked, the stationary double joint 41 can be pivoted around the axis of symmetry 36 of the chuck 34, designated hereinafter as the vertical pivot axis.

The first guide bar 46 is mounted on the stationary double joint 41 so that it can pivot around a first horizontal pivot axis. The second guide bar 47 is mounted on the stationary double joint 41 so that it can pivot around a second horizontal pivot axis 44. On the slidable double joint 51, the first guide bar 46 is mounted so that it can pivot around a third horizontal pivot axis 53 and the second guide bar 47 is mounted to pivot around a fourth horizontal pivot axis 54. The first horizontal pivot axis 43 and the second horizontal axis 44 on the stationary double joint 41 and the third horizontal pivot axis 53 and the fourth horizontal pivot axis 54 on the slidable double joint 51 are parallel to one another. The distance between the first horizontal pivot axis 43 and the second horizontal pivot axis 44 on the stationary double joint 41 and the distance between the third horizontal pivot axis 53 and the fourth horizontal pivot axis 54 on the slidable double joint 51 are equal. The distance, defined by the first guide bar 46, of the first horizontal pivot axis 43 on the stationary double joint 41 and the third horizontal pivot axis 53 on the slidable double joint 51 and the distance, defined by the second guide bar 47, of the second horizontal pivot axis 44 on the stationary double joint 41 and the fourth horizontal pivot axis on the slidable double joint 51 are equal. As a result, the horizontal pivot axes 43, 44, 53, 54 in every position of the guide bars 46, 47 form the corners of a parallelogram. The guide bars 46, 47 can pivot around the horizontal pivot axes 43, 44 in the partly vertical direction indicated by arrows 57. The slidable double joint 51 is correspondingly slid thereby.

A tension spring 59 in the form of a spiral spring is positioned between the guide bars 46, 47. The guide bars 46, 47 each comprise, in particular, a U-shaped cross-section and are positioned in such a way that they overlap, as indicated in FIG. 1 by broken lines. The tension spring 59 in particular is positioned in the hollow space surrounded by the two U-shaped guide bars 46, 47.

The second horizontal guide bar 47 includes a lock for direct locking of the fourth horizontal pivot axis 54 on the slidable double joint 51, and thus for direct locking of the slidable double joint 51 and direct locking of the stationary double joint 41 and first horizontal pivot axis 43, second horizontal pivot axis 44 and third horizontal pivot axis 53. Two push-buttons 56, of which only one is visible in FIG. 1, are positioned on the second horizontal guide bar 47 to release the lock of the fourth horizontal pivot axis 54.

The adjustable holding apparatus 10 further includes a first horizontal arm segment 60, which is connected with the distal end of the arm segment 40, configured as a parallelogram link, to pivot around a first vertical pivot axis 61. The first vertical pivot axis 61 of the first horizontal arm segment 60 is defined by a first vertical axle 63, which is positioned on the pivotable double joint 51 and in particular is rigidly connected with it, and by a first joint device 64 on the first horizontal arm segment 60. The first joint device 64 is, in particular, rigidly connected or integrated with the first horizontal arm segment 60. The second vertical axle 73 is, in particular, mounted in the second joint device 74 by means of a sliding or roller bearing. The first joint device 64 is connected with the first vertical axle 63, for example by a sliding or roller bearing. The first vertical pivot axis 61, in particular, is defined by the axis of symmetry of the first vertical axle 63 and of the bearing in the first joint device 64.

The first joint device 64 includes a lock for locking the first vertical axle 63 in the first joint device 64. Positioned on the first joint device 64 are two push-buttons 66 to release a lock of the first joint device 64, of which only one is visible in FIG. 1.

The adjustable holding apparatus 10 further includes a second horizontal arm segment 70, which is connected with the first horizontal arm segment 60 to pivot around a second vertical pivot axis 71. The second vertical pivot axis 71 of the second horizontal arm segment 70 is defined by a second vertical axle 73, which is in particular rigidly connected with the distal end of the first horizontal arm segment 60, and a second joint device 74 on the second horizontal arm segment 70. The second joint device 74 is, in particular, rigidly connected or integrated with the proximal end of the [translator note: "of the" is missing in the German but necessary] second horizontal arm segment 70. The second vertical axle 73 is in particular mounted in the second joint device 74 by means of a sliding or roller bearing. The second vertical pivot axis 71 is in particular defined by the axis of symmetry of the second vertical axle 73 and of the bearing in the second joint device 74.

The second joint device 74 includes a lock for locking the second vertical axle 73 in the second joint device 74. Two push-buttons 76 for releasing the lock, only one of which is visible in FIG. 1, are positioned [translator note: "positioned" is missing in German here but is included in similar sentences above] on the second joint device.

The adjustable holding apparatus 10 further includes a third horizontal arm segment 80, which can pivot in relation to the distal end of the second horizontal arm segment 70 around a third vertical pivot axis 81. The third vertical pivot axis 81 is defined by a third vertical axle 83, which is, in particular, rigidly connected with the third horizontal arm segment 80, and a third joint device 84 on the second horizontal arm segment 70 or determined by the axis of symmetry of the third vertical axle 83 and the third joint device 84. The third joint device 84 is, in particular, rigidly connected or integrated with the distal end of the second horizontal arm segment 70. The third vertical axle 83 is, in particular, mounted in the third joint device 84 by means of a sliding or roller bearing.

The third joint device 84, similarly as the first joint device 64, can be locked on the first horizontal arm segment 60 and the second joint device 74 on the second horizontal arm segment and comprises two push-buttons 86 to manually release the lock, of which only one is visible in FIG. 1. The third joint device 84 is positioned on the distal end of the second horizontal arm segment 70. The third vertical axle 83 is positioned on the third horizontal arm segment 80.

On the third horizontal arm segment 80, in particular close to the distal end of the third horizontal arm segment 80, a control valve 88 is further positioned that can be actuated manually by means of one or two push-buttons.

The adjustable holding apparatus 10 further includes an additional distal arm segment 90, whose proximal end is connected by a ball joint 91 with the distal end of the third horizontal arm segment 80. The distal arm segment 90 includes two unlocking levers 92 that are situated opposite one another and are mechanically coupled with a beaker-shaped clamping piece 93 that is positioned in the distal arm segment 90. The beaker-shaped clamping piece 93 is pressed by a spring, not shown in FIG. 1, or other elastic element against the surface of a ball of the ball joint 91 that is connected with the distal end of the third horizontal arm segment 80, in order to lock the ball joint 91. By actuating, in particular pressing together, the two unlocking levers 92, the beaker-shaped clamping piece 93 can be raised from the surface of the ball of the ball joint 91 in order to release the lock of the ball joint 91.

The distal arm segment 90 comprises a coupling 94 on its distal end. The distal arm segment 90 is releasably connected by the coupling 94 with a clamping device 100. Instead of the clamping device 100, described hereinafter, another clamping device, an adapter or other device for holding an endoscope or other medical device can be connected by the coupling 94 with the distal arm segment 90.

The clamping device 100 includes a stationary gripping jaw 101 and a movable gripping jaw 102. The movable gripping jaw 102 is rigidly connected with a gripping lever 103 or integrally configured with it. The movable gripping jaw 102 and the gripping lever 103 can pivot around a pivot axis 105. A spring, not shown in FIG. 1, or other elastic element presses the movable gripping jaw 102 against the stationary gripping jaw 101. By actuating, in particular pressing, the gripping lever 103, the movable gripping jaw 102 can be moved away from the stationary gripping jaw 101, against the spring force.

In the depiction in FIG. 1, by way of example, the circular cross-section of a shaft of an endoscope 16 is shown clamped between the stationary gripping jaw 101 and the movable gripping jaw 102. In order to be able to hold the endoscope clamped in different orientations between the stationary gripping jaw 101 and the movable gripping jaw 102, a profile element, approximately adapted to the cross-section of the endoscope 10, can be mounted on the stationary gripping jaw 101 and/or on the movable gripping jaw 102 so that it can rotate around an axis situated perpendicular to the longitudinal axis of the endoscope 10 and in the plane of projection of FIG. 1

The adjustable holding apparatus 10 comprises a series of degrees of freedom. Part of these degrees of freedom are designed for coarse adjustment. Additional degrees of freedom are foreseen for fine adjustment of the adjustable holding apparatus 10.

The clamping device 22 on the holding segment 20, the tensioning device 28 on the vertical tube 24 and the chuck 34 on the vertical arm segment 30 are provided in particular for coarse adjustment. The holding segment 20 can be fastened and locked at virtually any desired point on a fastening track 14 on an operating table by means of the clamping device 22. The vertical arm segment 30 can be vertically slid in the vertical tube 24 of the holding segment 20 and locked at an adjustable height with the tensioning device 28. The tensioning device 28, for example in similar manner to a quick release, is configured on a seat post of a bicycle. The lower end of the stationary double joint 41 of the arm segment 40 configured as a parallelogram link can be inserted into the chuck 34 and rotated around the vertical pivot axis 36. The arm segment 40 configured as a parallelogram link can be locked with respect to a rotation around the vertical pivot axis 36 by means of the chuck 34.

The additional degrees of freedom of the adjustable holding apparatus 10 are configured primarily for fine adjustment. For this purpose the joint devices can be locked, primarily together, on the third horizontal arm segment 80 by means of a central control element such as the aforementioned control valve 88 or each can be individually locked or the locks can be released again. To release the lock of a single joint 51, 64, 74, 84, the push-buttons 56, 66, 76, 86 and the unlocking lever 92 are provided in particular. The locking and releasing of the lock by means of the control valve 88 or by pressing the push-buttons 56, 66, 76, 86 are described in greater detail below with reference to FIGS. 3 and 4.

The pressure spring 59 is configured and positioned in such a way that it compensates the weight impact of the guide bars 46, 47 of the movable double joint 51, of the horizontal arm segments 60, 70, 80, of the distal arm segment 90, of the clamping device 100 and of the endoscope 16 partly, essentially completely, or completely. Even when all locks of the joints 41, 51, 64, 74, 84, 91 are released, the adjustable holding apparatus 10 nevertheless will not therefore modify, or at best will only slowly modify, its spatial shape or configuration or alignment. Medical staff, who want to move the adjustable holding apparatus 10 and, to do so, release the locks of all or almost all joints, must not therefore at the same instant abruptly compensate the weight impact of the holding apparatus 10 and of the endoscope 16. Because of the vertical arrangement of the pivot axes 61, 71, 81, the center of gravity has no impact on these degrees of freedom. Because of the configuration of the arm segment 40 as a parallelogram link, this holds true regardless of the height of the holding apparatus 10 or of its distal end selected by means of the arm segment 40 that is configured as a parallelogram link.

Figure 2:
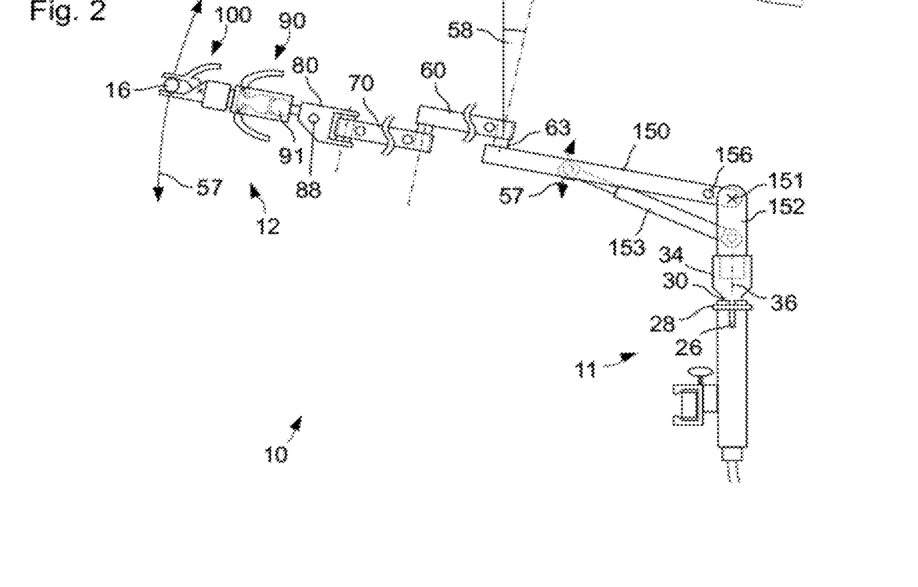
FIG. 2 shows a schematic depiction of a second adjustable holding apparatus.

FIG. 2 shows a schematic depiction of an additional adjustable holding apparatus 10, which in some characteristics resembles the adjustable holding apparatus described above with reference to FIG. 1. Some characteristics in which the adjustable holding apparatus 10 shown in FIG. 2 resembles the holding apparatus presented above with reference to FIG. 1 are not labeled with reference numbers in FIG. 2 and are also not described hereinafter in any further detail.

The adjustable holding apparatus 10 shown in FIG. 2 is distinguished from the holding apparatus presented before with reference to FIG. 1, in particular, in that instead of an arm segment configured as a parallelogram link for height adjustment, an arm segment is provided that is rigidly connected with the axle 63 and that can pivot around a horizontal pivot axis 151 of a jointed body 152. The jointed body 152—similarly as in the example of the stationary double joint presented with reference to FIG. 1—can be inserted in a chuck 34, pivoted therein around a vertical pivot axis 36, and locked by the chuck 34 with respect to the vertical pivot axis 36.

The ability of the arm segment 150 to pivot around the horizontal pivot axis 151 can be locked. For selective manual release of the lock of the arm segment 150, two push-buttons 156 similar to the push-buttons described above in connection with the embodiment in FIG. 1 are foreseen. Of the two push-buttons situated opposite one another, only one can be seen in FIG. 1.

A pressure spring 153, for example a gas pressure spring, supports the arm segment 150 with respect to the jointed body 152. Owing to the rigid arrangement of the first vertical axle 63 on the arm segment 150, a height adjustment of the distal end 12 of the adjustable holding apparatus 10, and thus for example of an endoscope 16 held on the distal end 12 of the adjustable holding apparatus 10, is possible primarily by means of a common pivoting of the arm segment 150 and the other arm segments 60, 70, 80 around the horizontal pivot axis 151. An additional, limited height adjustment—similarly as in the example presented above with reference to FIG. 1—is possible by the ball joint 91.

The pressure spring 153 is configured and positioned to compensate substantially or completely the weight impact of the adjustable holding apparatus—in particular the weight impact of the arm segments 150, 60, 70, 80, 90 of the clamping device 100 and of the endoscope 16. It can be recognized that owing to a pivoting in the essentially vertical direction indicated by arrows 57, a displacement of the height of the distal end 12 of the adjustable holding apparatus 10 and of an endoscope 16 held there is possible in a relatively large range with a relatively small departure 58 of the pivot axes 61, 71, 81 from the vertical. Because of the relatively small departure 58 of the pivot axes 61, 71, 81 from the vertical, the center of gravity has only a minor impact on the corresponding degrees of freedom.

On the whole, therefore, the adjustable holding apparatus presented here with reference to FIG. 2 makes possible, even with completely released stops of all joints, for medical staff to apply relatively small holding forces in order to prevent movement of the adjustable holding apparatus. In any case, with the adjustable holding apparatus presented with reference to FIG. 2, contrary to the holding apparatuses mentioned in the introduction with several ball joints, even with the locks on all joints completely released, it is still necessary as a rule to compensate a fraction of the weight impact manually.

With another embodiment that is an alternative to the embodiments in FIGS. 1 and 2, but not shown in drawings here, a vertical linear guide is provided to shift the height of the adjustable holding apparatus. For example, a vertical arm segment 30, similar to the vertical arm segment 30 from FIG. 1 or FIG. 2, is configured as telescopable. As compensation device for to at least partially compensate the weight of the adjustable holding apparatus, a gas pressure spring, for example, is foreseen in the interior of the vertical arm segment.

In the embodiments of FIGS. 1 and 2, an attachment to a fastening track 14 is provided in each case. Alternatively, a similar adjustable holding apparatus can be configured for direct or indirect fastening to a ceiling of an operating room or other room. In particular, an adjustable holding apparatus can be configured for attachment to a rigid or, on its own part, adjustable ceiling bracket.

For use in direct or indirect fastening to a ceiling of an operating room, the embodiments of FIGS. 1 and 2 can be applied with few modifications, for example by rotating them by 180 degrees around a horizontal axis or reflecting them on a horizontal plane, that is, inverting them, head down. In particular, this requires inverting of the effect of the tension spring 59 of the embodiment of FIG. 1 or of the pressure spring 153 of the embodiment of FIG. 2. This can be done by replacing the tension spring 59 with a pressure spring or the pressure spring 153 with a tension spring or by modifying the contact points of the tension spring 59 of the pressure spring 153.

As mentioned, the lower end of the stationary double joint is configured especially as a plug-in bolt with a cylindrical or essentially cylindrical portion. For direct or indirect attachment of an adjustable holding apparatus to a ceiling of an operating room, the essentially cylindrical portion can comprise a notch, a groove (in particular, a surrounding groove) or other concave section in order to make possible a form-locked fastening on a ceiling bracket.

Figure 3:
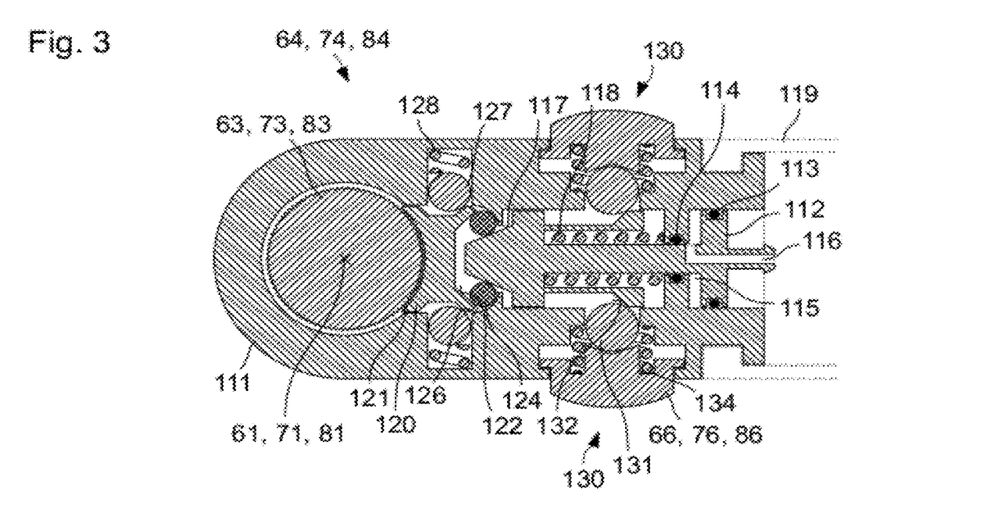
FIG. 3 shows a schematic depiction of a lockable joint.
Figure 4:
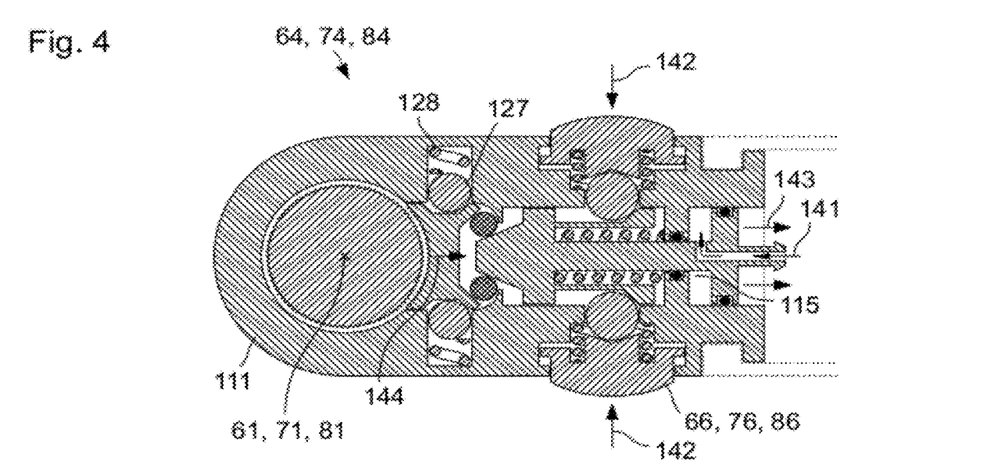
FIG. 4 shows an additional schematic depiction of the lockable joint from FIG. 3.

FIGS. 3 and 4 show schematic sectional depictions of an example of a joint device 64, 74, 84 to produce a vertical pivot axis 61, 71, 81 of the adjustable holding apparatus described above with reference to FIG. 1 or of the corresponding approximately vertical pivot axes of the adjustable holding apparatus from FIG. 2. The sectional planes shown in FIGS. 3 and 4 are perpendicular to the plane of projection of FIGS. 1 and 2 and perpendicular to the pivot axes 61, 71, 81.

A joint device on one of the horizontal axes 43, 44, 53, 54 of the arm segment 40 of the adjustable holding apparatus from FIG. 1, configured as a parallelogram link, and a joint device on the horizontal pivot axis 151 of the arm segment 150 of the adjustable holding apparatus from FIG. 2 are, in particular, also of similar structure.

FIG. 3 shows a joint device 64, 74, 84 in locked condition; FIG. 4 shows the joint device 64, 74, 84 with lock released. Most of the reference numbers referring to characteristics and components of the joint device 64, 74, 84 are contained only in FIG. 3. FIG. 4 contains additional reference numbers that refer to the function of the joint device 64, 74, 84, in particular to movements of its components.

The joint device 64, 74, 84 includes a housing 111 and a power drive device 112 in the housing 111. The power drive device 112 includes a piston-shaped portion that is mounted so that it can slide linearly in a corresponding cylindrical hollow space of the housing 111. An O-ring insulation 113 is provided between an external periphery of the piston-shaped portion of the power drive device 112 and the opposite inner wall of the housing 111 [translator note: original had 121, used elsewhere and incorrect for the housing]. Another O-ring insulation 114 is positioned between a rod-shaped portion of the power drive device 112 and the housing 111 of the joint device 64, 74, 84. The housing 111 and the piston-shaped portion of the power drive device 112 enclose a hollow space 115 with variable volume, which is insulated by the O-ring insulations 113, 114.

The power drive device 112 is provided with a hose nipple 116, by which compressed air or another fluid can be conducted into the hollow space 115 or diverted from it. In addition, sliding surfaces 117 are provided on the power drive device 112. A pressure spring 118 is positioned between the power drive device 112 and the housing 111 in such a way that it presses the power drive device 112 to the left on the basis of the depictions in FIGS. 3 and 4.

On the right side, based on depictions in FIGS. 3 and 4, the housing is joined, in form-locked or else force-fitted or firmly bonded manner, with an end of a tubular segment 119, indicated in broken lines, of an arm segment.

The joint device 64, 74, 86 further includes a locking device 120 with a corrugated surface 121 and sliding surfaces 122. A sliding body 124 is positioned between each sliding surface 117 on the power drive device 112 and a sliding surface 122 on the locking device 120. The sliding body 124, in particular, is a cylindrical rod whose cylinder axis is perpendicular to the plane of projection of the drawing. For each sliding body, a guide 126 in the form of an additional sliding surface is provided on the housing 111. The sliding surface 117 on the power drive device 112 and the sliding surface 122 on the locking device 120, between which a sliding body 124 is positioned, are not parallel to one another but rather are at a distance that widens in the direction toward the guide 126.

On opposite sides of the locking device 120, balls 127 are positioned that are pressed by springs 128 against non-parallel portions of the side surfaces of the locking device 120. Because of the inclination of the aforementioned portions of the side surfaces of the locking device 120, the springs exert a force via the balls 127 that, based on the depictions in FIGS. 3 and 4, acts toward the right.

The joint device 64, 74, 84 further includes two symmetrically arranged unlocking devices 130. An unlocking device 130 includes in each case a ball 131 that can be contiguous with an additional sliding surface 132 on the power drive device 112. The ball 131 is positioned in each case between one of the push-buttons 56, 66, 76 mentioned above in conjunction with FIGS. 1 and 2 and the sliding surface 132 on the power drive device 112. In each case a pressure spring 134 between the housing 111 and the push-button 56, 66, 76 pushes the push-button 56, 66, 76 toward the outside.

FIG. 3 shows the joint device 64, 74, 84 in a configuration or condition in which neither a more than non-essential pressure is exerted on one of the push-buttons 56, 66, 76 nor an essentially higher pressure in comparison with the ambient pressure is present in the hollow space 115 between the piston-shaped portion of the power drive device 112 and the housing 111. In this condition, the pressure spring 118 presses the power drive device 112 to the left, on the basis of the depictions in FIGS. 3 and 4. By means of a gear that is formed by the sliding surfaces 117 on the power drive device 112, the sliding bodies 124 and the sliding surfaces 122 on the locking device 120, this force is transmitted to the locking device 120 that is pressed against the axle 63, 73, 83.

Owing to the corrugation of the surface of the axle 63, 73, 83 and the corrugation of the surface 121 on the locking device 120, the locking device 120 locks the axle 63, 73, 83 and the joint device 64, 74, 84 with respect to one another in the condition shown in FIG. 3. If a rotary moment, based on the pivot axis 61, 71, 81 is exerted between the axle 63, 73, 83 and the joint device 64, 74, 84, the locking device 120 is pressed toward the right in the direction indicated by arrow 144 on the basis of the depictions in FIGS. 3 and 4 by the corrugations that are engaged.

The aforementioned gear 122 formed by the sliding surfaces 117 on the power drive device 112, the sliding bodies 124 and the sliding surfaces 122 on the locking device 120 is configured to act as a blocking gear. The force that is to be applied by the pressure spring 118 to maintain the locking is therefore smaller or markedly smaller than the force that holds the locking device 120 in the locking position shown in FIG. 3. For this purpose, in particular, the sliding surfaces 117 on the power drive device 112, the sliding bodies 124 and the sliding surfaces 122 on the locking device 120 are correspondingly configured with respect to material, surface qualities and relative orientation.

FIG. 4 shows the joint device 64, 74, 84 in a condition or configuration in which the power drive device 112 is slid toward the right, based on the depiction in FIG. 3. This sliding toward the right can be caused by an influx of compressed air into the hollow space 115 and a resulting difference in pressure between the inlet 141 and the environment amounting to, or exceeding, a predetermined minimum quantity. Alternatively, the sliding of the power drive device 112 toward the right can be caused by pressure 142 on one or both of the press-buttons 56, 66, 76, 86 situated opposite. The pressure 142 against a force of the particular pressure spring 134 slides the ball 131 to the power drive device 112. By reciprocal action of the ball 131 with the sliding surface 132 on the power drive device 112, the power drive device 112 is pushed toward the right in the direction indicated by arrows 143.

Owing to the sliding of the sliding surfaces 117 on the power drive device 112 toward the right, the sliding bodies 124 can move toward one another. The sliding bodies 124 therefore apply no force, or only a minor force, against the sliding surfaces 122 on the locking device 120. Therefore the balls 127 pressed by the springs 128 against diagonal portions of the side surfaces of the locking device 120 can slide the locking device 120 out of the locking position toward the right. The reciprocal locking of the axle 63, 73, 83 and the joint device 64, 74, 84 is thereby released.

The balls 127 and springs 128 can be dispensed with under some conditions, because for example if there is a corrugation of the surface 121 of the locking device 120 and of the surface of the axle 63, 73, 83 with a triangular profile with diagonal flanks, a rotary moment between the axle 63, 73, 83 and the joint device 64, 74, 84 already suffices to slide the locking device 120 toward the right when the power drive device 112 likewise is slid toward the right.

A gear consisting of one or more sliding bodies 124, which each are positioned between a sliding surface 117 on the power drive device 112 and a sliding surface 122 on the locking device 120 and are led by a guide 126, allows a transmission of a relatively small force exerted by the power drive device 112 with a relatively large path into a greater force with smaller path on the locking device 120. As already mentioned, with the use of the friction between the sliding bodies 124 and the sliding surfaces 117, 122 and the guide 126, it is possible to achieve a behavior of a blocking gear in which the dissolving of the lock requires a force that, in proportion to the force exerted by the pressure spring 118 on the power drive device 112, far exceeds the simple transmission ratio that results, in the friction-free case, from the geometry of the sliding bodies 124 and of the sliding surfaces 117, 122 and the guide 126.

The cross-section of the housing 111 and the cross-section of the power drive device 112 are each shown as single units in FIGS. 3 and 4. Even for the sake of an optimized production expense, it can be necessary or advantageous to compose the housing 111 of several parts. It can be especially meaningful to produce the housing 111 in the area of the guide 126 of a hard, friction-resistant material and to insert one or more corresponding components in the housing 111.

In the example presented with reference to FIGS. 3 and 4, the pressure spring 118 and the power drive device 112 together form a power drive for the lock. Locking occurs through the force of the pressure spring 118, and release of the lock occurs pneumatically or hydraulically. Instead of a pneumatic or hydraulic power drive, an electro-mechanical or linear-magnetic power drive, for example, can be provided. With corresponding arrangement, this drive can be foreseen either for locking and for release of the locking or only for locking (against the force of a spring that releases the lock) or only for releasing the lock (against the force of a locking spring).

For simultaneous release of the locks on all joint devices 64, 74, 84, the hose nipples 116, for example, are connected by hoses with one another and connected with the control valve 88 shown in FIGS. 1 and 2. The control valve 88 is configured in such a way that compressed air can be conducted into the hollow spaces to release the lock 115 and can be released from them to lock it. The hoses or tubes required for this are not shown in FIGS. 1 and 2 and can be positioned at least partly in the arm segments 40, 60, 70, 80, 90.

In the embodiments in FIGS. 1 and 2, the locking of the ball joint 91 on the distal arm segment 90 can be released only manually by the unlocking levers 92, which act on the beaker-shaped clamping piece 93. In addition, in the embodiment of FIGS. 1 and 2, the vertical pivot axis 36, which is defined by the chuck 34 and the lower end of the stationary double joint 41 or joint body 152, which in particular is configured as a plug-in bolt, can be locked only manually by means of the chuck 34. This locking also can be released only by manual actuation of the chuck 34. Both embodiments in FIGS. 1 and 2, alternatively, can be configured in such a way that also the release of the lock of the ball joint 91 and/or the release of the lock of the vertical pivot axis 36 is possible by means of the control valve 88.

In particular when the locking of the ball joint 91 can also be released by means of the control valve 88, it can be advantageous to arrange the control valve and one or more push-buttons for its actuation on the distal arm segment 90, for example instead of the unlocking lever 92. In this case the ball joint 91, similarly as presented above with reference to FIGS. 3 and 4, can be actuated by a gear, such that the lock is released by means of compressed air. Alternatively, the unlocking levers 92 are configured to act simultaneously directly on the beaker-shaped clamping piece 93 and on the control valve. In any case it can be advantageous to provide a possibility for direct manual release of the lock of the ball joint 91, which acts without compressed air.

If the lock of the vertical pivot axis 36, which in the embodiments in FIGS. 1 and 2 is defined by the chuck 34 and the lower end of the stationary double joint 41 or of the joint body 152, is intended to be controllable by means of the control valve 88, then instead of a chuck, a device similar to the lockable joint presented above with reference to FIGS. 3 and 4 can be provided. Here too a possibility for direct manual release of the lock without compressed air can be advantageous.

What is claimed is:

1. An adjustable holding apparatus comprising:
a proximal end;
a distal end, the distal end having a device for holding an endoscope or a medical device;
a plurality of arm segments between the proximal end and the distal end of the holding apparatus;
a plurality of lockable joints, each lockable joint connects two of the plurality of arm segments with one another in a jointed fashion, each lockable joint having an axle disposed therein, each axle being fixed relative to its associated lockable joint when the lockable joint is in a locked position, each axle being rotatable relative to its associated lockable joint when the lockable joint is in a released position;
a compensation device for at least partial compensation of the weight impact of the holding apparatus in a manual pivoting or sliding motion of at least one arm segment in a vertical direction;
a plurality of locking devices each associated with a lockable joint for locking the joint;
a plurality of pneumatically controlled power drive devices each associated with a lockable joint and configured to actuate the locking device between a locked position corresponding to the locked position of the lockable joint and a released position corresponding to the released position of the lockable joint; and
a control valve in communication with each pneumatically controlled power drive device so that an actuation of the control valve simultaneously biases each of the locking devices between a locked position and a released position;
wherein each lockable joint comprises a gear that transmits a smaller force and a greater path on the power drive device into a greater force and a smaller path on the locking device.

2. The adjustable holding apparatus of claim 1, wherein the compensation device includes no mechanical power drive.

3. The adjustable holding apparatus of claim 1, wherein the gear is a locking mechanism.

4. The adjustable holding apparatus of claim 1, wherein each lockable joint further includes a spring or other elastic element that is coupled with the locking device in such a way that a force exerted by the spring or other elastic element causes a locking of the joint.

5. The adjustable holding apparatus of claim 1, wherein the gear includes a sliding surface on the locking device, a sliding surface on the power drive device, a guide and a sliding piece that is contiguous with the sliding surface of the locking device and with the sliding surface of the power drive device and is led by the guide.

6. The adjustable holding apparatus of claim 5, wherein an arm segment of the plurality of arm segments is in the shape of a parallelogram link.

7. The adjustable holding apparatus of Claim 6, wherein the compensation device includes a spring or other elastic element.

8. The adjustable holding apparatus of claim 1, wherein one or more arm segments of the plurality of arm segments are configured to pivot only around vertical or essentially vertical axes.

9. The adjustable holding apparatus of claim 1, wherein a joint is configured on a predetermined arm segment to make possible a pivoting around a horizontal axis and wherein additional joints are each configured for pivoting around an axis that is perpendicular to the horizontal axis.

10. The adjustable holding apparatus of claim 1 further comprising an unlocking device with a push-button that is associated with a single lockable joint to release the locking of the associated lockable joint by manual pressure on the push-button.

11. The adjustable holding apparatus of claim 10 further comprising a plurality of unlocking devices, each unlocking device is associated with a lockable joint.

* * * * *